United States Patent
Burkett et al.

(10) Patent No.: US 9,228,965 B2
(45) Date of Patent: Jan. 5, 2016

(54) SYSTEMS AND METHODS FOR SINGLE-SENSOR OIL QUALITY MEASUREMENT

(71) Applicant: HENNY PENNY CORPORATION, Eaton, OH (US)

(72) Inventors: Douglas A. Burkett, Eaton, OH (US); Edmond L. Phillipps, Jr., Cincinnati, OH (US)

(73) Assignee: Henny Penny Corporation, Eaton, OH (US)

( * ) Notice: Subject to any disclaimer, the term of this patent is extended or adjusted under 35 U.S.C. 154(b) by 520 days.

(21) Appl. No.: 13/651,965

(22) Filed: Oct. 15, 2012

(65) Prior Publication Data
US 2013/0036916 A1   Feb. 14, 2013

Related U.S. Application Data

(63) Continuation-in-part of application No. 13/215,158, filed on Aug. 22, 2011, now Pat. No. 8,847,120, and a continuation-in-part of application No. PCT/US2012/054231, filed on Sep. 7, 2012.

(60) Provisional application No. 61/375,851, filed on Aug. 22, 2010, provisional application No. 61/532,715, filed on Sep. 9, 2011.

(51) Int. Cl.
*G01N 27/06* (2006.01)
*G01N 27/22* (2006.01)
(Continued)

(52) U.S. Cl.
CPC ............. *G01N 27/07* (2013.01); *A47J 37/1266* (2013.01); *G01N 27/06* (2013.01); *G01N 33/03* (2013.01)

(58) Field of Classification Search
None
See application file for complete search history.

(56) References Cited

U.S. PATENT DOCUMENTS

| 3,047,797 A | 7/1962 | Borsboom |
| 3,432,750 A | 3/1969 | Botstiber |

(Continued)

FOREIGN PATENT DOCUMENTS

| EP | 0426012 A2 | 5/1991 |
| EP | 0501682 A2 | 9/1992 |

(Continued)

OTHER PUBLICATIONS

European Patent Office, International Search Report and Written Opinion for International Application No. PCT/US2011/048701 (counterpart to parent of above-captioned patent application), mailed Dec. 5, 2011.

(Continued)

*Primary Examiner* — Joseph M Pelham
(74) *Attorney, Agent, or Firm* — Baker Botts L.L.P.

(57) ABSTRACT

A cooking medium filter system determines a quality of a cooking medium. The cooking medium filter system includes a filter container, a filter medium, a pump, a sample chamber, and a controller. The filter container receives the cooking medium from a cooking vessel. The filter medium is disposed in the filter container and removes contaminants from the cooking medium. The pump conveys the cooking medium along a filter path from the filter container to the cooking vessel. The sample chamber is disposed in the filter path downstream from the filter medium. The sample chamber includes an electrode disposed therein. The sample chamber receives therein a quantity of the cooking medium that is sufficient to immerse the electrode therein. The controller controls operations of the filter pump and controls the electrode to measure a property of the cooking medium that is associated with the quality of the cooking medium.

22 Claims, 8 Drawing Sheets

(51) Int. Cl.
  *G01N 27/07* (2006.01)
  *G01N 33/03* (2006.01)
  *A47J 37/12* (2006.01)

(56) References Cited

U.S. PATENT DOCUMENTS

| | | | | |
|---|---|---|---|---|
| 3,746,974 | A * | 7/1973 | Stoakes et al. | 324/686 |
| 4,646,070 | A * | 2/1987 | Yasuhara et al. | 340/603 |
| 5,071,527 | A * | 12/1991 | Kauffman | 205/786 |
| 5,339,254 | A | 8/1994 | Matlock et al. | |
| 5,463,321 | A | 10/1995 | Matlock et al. | |
| 5,594,327 | A * | 1/1997 | Sagredos et al. | 324/71.1 |
| 5,818,731 | A * | 10/1998 | Mittal et al. | 702/22 |
| 5,933,016 | A * | 8/1999 | Kauffman et al. | 324/698 |
| 6,274,850 | B1 | 8/2001 | Mercer | |
| 6,469,521 | B1 * | 10/2002 | Klun et al. | 324/658 |
| 6,600,306 | B1 * | 7/2003 | Pernot et al. | 324/71.1 |
| 7,504,836 | B2 * | 3/2009 | Chambon et al. | 324/698 |
| 7,612,874 | B2 * | 11/2009 | Kong et al. | 356/70 |
| 7,834,646 | B2 * | 11/2010 | Chambon et al. | 324/698 |
| 8,421,486 | B2 * | 4/2013 | Akiyama et al. | 324/698 |
| 8,497,691 | B2 * | 7/2013 | Behle et al. | 324/698 |
| 8,519,726 | B2 | 8/2013 | Sun | |
| 8,829,928 | B2 * | 9/2014 | Gonzalez et al. | 324/686 |
| 8,847,120 | B2 * | 9/2014 | Burkett et al. | 219/439 |
| 2003/0155935 | A1 * | 8/2003 | Klun | 324/664 |
| 2004/0045448 | A1 | 3/2004 | Abe et al. | |
| 2005/0212533 | A1 * | 9/2005 | Itomi | 324/698 |
| 2007/0040559 | A1 * | 2/2007 | Klun | 324/453 |
| 2008/0121115 | A1 * | 5/2008 | Tiszai et al. | 99/334 |
| 2008/0213445 | A1 * | 9/2008 | Feinberg et al. | 426/417 |
| 2009/0309619 | A1 * | 12/2009 | Behle et al. | 324/698 |
| 2011/0267080 | A1 * | 11/2011 | Hedges | 324/698 |
| 2013/0278276 | A1 * | 10/2013 | Behle et al. | 324/663 |

FOREIGN PATENT DOCUMENTS

| | | | | |
|---|---|---|---|---|
| EP | 1150119 | A1 | 10/2001 | |
| EP | 1947455 | A2 | 7/2008 | |
| JP | 2004-008255 | A | 1/2004 | |
| JP | 2004016798 | A * | 1/2004 | A47J 37/12 |

OTHER PUBLICATIONS

The International Bureau of WIPO, International Preliminary Report on Patentability for International Application No. PCT/US2011/048701, issued Feb. 26, 2013.

The International Bureau of WIPO, International Preliminary Report on Patentability for International Application No. PCT/US2012/054231, issued Mar. 12, 2014.

European Patent Office, International Search Report for International Application No. PCT/US2012/054231, mailed Jan. 2, 2013.

* cited by examiner

SYSTEMS AND METHODS FOR SINGLE-SENSOR OIL QUALITY MEASUREMENT

CROSS-REFERENCE TO RELATED APPLICATIONS

This application is a continuation-in-part application of U.S. patent application Ser. No. 13/215,158, filed on Aug. 22, 2011, which claims the benefit of U.S. Provisional Application No. 61/375,851, filed on Aug. 22, 2010, and International Patent Application No PCT/US2012/054231, filed on Sep. 7, 2012, which claims the benefit of U.S. Provisional Application No. 61/532,715, filed on Sep. 9, 2011, the disclosures of which are incorporated herein by reference in their entirety.

BACKGROUND OF THE INVENTION

1. Field of the Invention

The present invention relates generally to oil quality measurement and more specifically to systems and methods for single-sensor oil quality measurement.

2. Description of Related Art

When preparing food in a fryer, the quality of the cooking medium (e.g., the oil) may impact the quality of the food that is cooked by the fryer. As the cooking medium is used to cook food, particles of food may contaminate the cooking medium. The flavor characteristics of each of these food products may become infused to a greater or a lesser degree in the cooking medium. This infusion may adversely affect food quality. Moreover, upon heating the cooking medium, the cooking medium may undergo chemical reactions (e.g., hydrolysis, oxidation, and polymerization). These degradations may cause products such as free fatty acids, hydroperoxides, and polymerized triglycerides. Moreover, degradation may reduce the viscosity of the cooking oils, which also may decrease performance. In many instances, such degradation of the cooking medium does not become apparent to the human eye until a late stage of degradation. Thus, there is a need to measure the quality of the cooking medium, which directly correlates to its suitability for use in cooking.

One method of measuring the quality of cooking medium uses an electrode sensor immersed in the frying medium. The electrode is energized with an excitation voltage signal, and the resulting current flows from the energized electrode through the cooking medium to a ground. The measured value of this current corresponds to the cooking medium quality (e.g., the suitability of the cooking medium for use during cooking) Nevertheless, known electrode systems are not suitable for use in an open fryer. First, the construction materials must withstand cooking oil temperatures up to 450 degrees Fahrenheit (230 degrees Celsius). Second, the electrode must resist mechanical damage from cleaning and operator equipment abuse. Thus, the electrode must be sufficiently unaffected by contamination from suspended food particles, as well as from long-term varnishing by exposure to hot cooking medium.

In addition to the above problems, for use in a commercial fryer, known electrodes are not small enough to mount in the cooking vessel below the cooking medium level without interfering with the fry baskets or other mechanical features of the cooking vessel. Additionally, readouts from the electrodes must be sufficiently shielded such that they are sufficiently unaffected by the proximity of grounded metal objects in the cooking vessel (e.g., the fry baskets). Thus, the electrode must be small, but if the electrode is too small, then the electrode may not be capable of generating sufficient signal gain to generate an output signal of sufficient magnitude to resolve cooking medium quality differences with an adequate signal to noise ratio, Cooking media may have very high resistance, so the electrode current is very small, requiring a large circuit gain to create a usable signal.

Known electrodes use, for example, an interdigitated pattern of conductors deposited on a ceramic or a fiberglass substrate. These conductors have very small spacing. Such electrodes are too fragile for use in a commercial fryer. Additionally, such electrodes are too susceptible to contamination from food particles entering the small conductor spacing. Further, known electrodes, such as those described above, do not comply with food safety regulations.

Moreover, known systems for measurement of food cooking oil quality use, for example, a sensor in each vat of a fryer with multiple vats. In the known systems, the oil quality is monitored continuously. Further, in the known systems, the sensor is near the top of the vat but below a minimum level of oil required for proper operation of the known systems. This location reduces the risk of trapping contamination in the electrode gaps. In other known systems, each sensor is placed near the bottom of each vat, such that each sensor is fully immersed in the oil. In addition, in the known systems, the cooking media surrounding the sensor in each vat may be stationary or may engage in a negligible amount of motion related to convection, pressure, or other phenomena, such that the electrode is exposed to a static electric field and the current flow in the cooking media is steady. Further, the temperature of the cooking media at the electrode may be the desired cooking temperature and the measured conductivity does not have to be adjusted to compensate for a temperature difference.

SUMMARY OF THE INVENTION

Therefore, a need has arisen for systems and methods for a cooking apparatus that overcome these and other shortcomings of the related art. A technical advantage of the present invention may be that an electrode may be created that may comply with food safety regulations and may be durable enough for use in a commercial flyer. Moreover, the size and geometry of the electrode, the size and geometry of a sample chamber, and the position of the electrode within the sample chamber may determine the magnitude of the output response. As mentioned above, most cooking media may have a very high resistance. The electrode current then may be very small (e.g., on the order of micro-amps (µA) or nano-amps (nA)). Thus, a large circuit gain may be beneficial to create a usable signal. Nevertheless, artificially boosted circuit gains also may amplify the system noise, which may increase the need for signal filtering and processing, and which also may contribute to false readings. Thus, the electrode disposed in the sample chamber as disclosed herein may produce an increased signal output therefrom. The inherent output response from the electrode when a cooking medium of a given quality is applied to the electrode is referred to as "electrode gain." The electrode may be of a particular size, geometry, design, and construction and may be disposed in a sample chamber of a particular size, geometry, design, and construction, such that a high electrode gain is provided from the electrode. The specific values in this invention have been carefully tested to provide high electrode gain as an unexpected result.

Another technical advantage of the present invention may be that a single oil quality sensor may be located in the oil filter system line of a fryer, which may reduce costs and improve reliability. The sensor location may have the advantage that the sampled oil may be less contaminated with particulates than the oil in a vat because the oil has already passed through the filter media. Further, the oil quality sensor may not be exposed to the harsh physical conditions within the vat and may not experience damage, such as, for example, physical damage caused by equipment operators during processes such as scraping dun rig vat cleaning. In addition, the present invention may reduce costs and improve reliability by replacing multiple vat sensors with a single sensor located in the oil filter system line that may be used to determine the oil quality of each of the multiple vats.

Still another technical advantage of the present invention may be that a sample chamber including the oil quality sensor therein and configured to receive oil therein, also may be of a particular size, geometry, design, and construction in order to provide high electrode gain. Consequently, the particular size, geometry, design, and construction of the sample chamber and the location of the oil quality sensor in the oil filter, rather than in the vat, may permit an electrode to be used without a guard ring, while maintaining the electrode gain typically associated with a guard ring.

A cooking medium filter system disclosed herein may be configured to determine a quality of a cooking medium. The cooking medium filter system may include a filter container, a filter medium, a pump, a sample chamber, and a controller. The filter container may be configured to receive the cooking medium from a cooking vessel. The filter medium may be disposed in the filter container, Further, the filter medium may be configured to remove contaminants from the cooking medium received in the filter container. The pump may be configured to convey the cooking medium along a filter path from the filter container to the cooking vessel. The sample chamber may be disposed in the filter path downstream from the filter medium. Further, the sample chamber may have an electrode disposed therein. Moreover, the sample chamber may be configured to receive therein a quantity of the cooking medium. The quantity of the cooking medium may be sufficient to immerse the electrode therein. The controller may be configured to control operations of the filter pump. Further, the controller may be configured to control the electrode to measure a property of the cooking medium. The property may be associated with the quality of the cooking medium.

A method for monitoring a quality of a cooking medium conveyed through a cooking medium filter system may include certain processes. The method for monitoring the quality of the cooking medium may include receiving the cooking medium in a filter container from a cooking vessel. The method for monitoring the quality of the cooking medium may include activating a pump to convey the cooking medium along a filter path from the filter container to the cooking vessel. The method for monitoring the quality of the cooking medium may include removing contaminants from the received cooking medium. The method for monitoring the quality of the cooking medium may include receiving in a sample chamber a quantity of the cooking medium. The quantity of cooking medium may be sufficient to immerse therein an electrode disposed in the sample chamber. The method for monitoring the quality of the cooking medium may comprise measuring a property of the cooking medium in the sample chamber with the electrode. The property may be associated with the quality of the cooking medium.

A fryer system disclosed herein may be configured to determine a quality of a cooking medium. The fryer may include a cooking vessel, a cooking medium filter system, and a controller. The cooking vessel may be configured to receive the cooking medium therein. The cooking medium filter system may be configured to filter the cooking medium. The cooking medium filter system may include a filter container, a filter medium, a pump, and a sample chamber. The filter container may be configured to receive the cooking medium from the cooking vessel. The filter medium may be disposed in the filter container. The filter medium may be configured to remove contaminants from the cooking medium received in the filter container. The pump may be configured to convey the cooking medium along a filter path from the filter container to the cooking vessel. The sample chamber may be disposed in the filter path downstream from the filter medium. The sample chamber may include an electrode and a temperature sensor disposed therein. The sample chamber may be configured to receive therein a quantity of the cooking medium. The quantity of the cooking medium may be sufficient to immerse the electrode and the temperature sensor therein. The controller may be configured to control the pump to pause conveyance of the cooking medium along the filter path for a particular period of time when the electrode and the temperature sensor are immersed in the cooking medium. Further, the controller may be configured to control the temperature sensor to measure a temperature of the cooking medium during the particular period of time. In addition, the controller may be configured to control the electrode to measure a conductivity of the cooking medium during the particular period of time. Moreover, the controller may be configured to determine the quality of the cooking medium at a particular temperature based on the measured temperature of the cooking medium and the measured conductivity of the cooking medium during the particular period of time.

Other objects, features, and advantages of the present invention will be apparent to persons of ordinary skill in the art in view of the foregoing detailed description of the invention and the accompanying drawings.

BRIEF DESCRIPTION OF THE DRAWINGS

For a more complete understanding of the present invention, needs satisfied thereby, and the objects, features, and advantages thereof, reference now is made to the following description taken in connection with the accompanying drawings.

DETAILED DESCRIPTION OF EMBODIMENTS OF THE INVENTION

Figure 1:
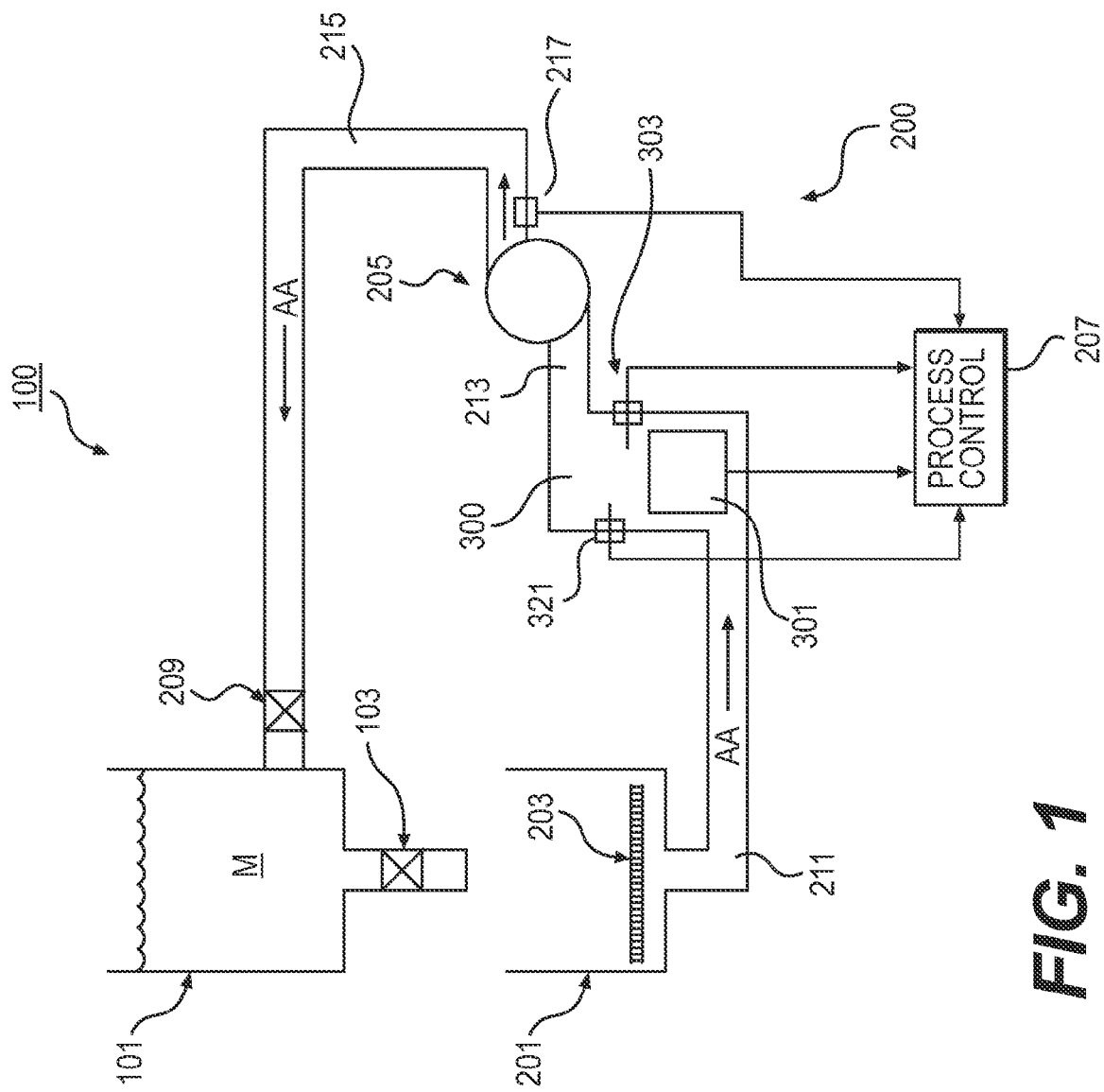
FIG. 1 is a schematic view of a fryer system comprising a cooking vessel and a filter system.

As noted above, existing systems for measurement of food cooking oil quality may typically use a sensor in each vat of a fryer with multiple vats. To reduce cost and improve reliability, it may be desirable to replace the multiple vat sensors with a single sensor located in an oil filter system line (e.g., after the filter media). This sensor location may have the advantage that the sampled oil may be less contaminated with particulates than oil in one or more of the multiple vats because the oil has already passed through the filter media.

Nevertheless, there are some disadvantages to replacing the multiple vat sensors with the single sensor located in the oil filter system line. In contrast to the in-vat sensors, the oil may only be sampled while it is in the oil filter system line (e.g., flowing past the sensor, stagnating in the oil filter system line), such as during a periodic filter activity. Further, measurement error may be prevented or reduced by fully immersing the sensor in the oil. Because oil conductivity may be a strong function of oil temperature and oil quality, one or more of heating the oil in the oil filter system line to cooking temperature and compensating for the difference in temperature of the oil and the cooking temperature may improve the accuracy of the quality determined from the measured conductivity. Because the oil may not be stationary during a typical oil filter process and may instead flow past the sensor, the accuracy of the measured conductivity and the resultant quality of the oil may be improved by briefly stopping the oil flow, which may permit the sensor to acquire an accurate measurement of the conductivity.

Such problems may be avoided or reduced mounting the sensor in a small chamber or tank along the oil filter system tine. The sample chamber may be designed to trap as little oil as possible, so that most of the filtered oil may be returned to the cooking vat. Such a sample chamber may allow the oil to completely cover the sensor quickly and reliably, so that the sensor may make accurate conductivity measurements without significantly increasing the time required for the filter process.

Further, even though the sampled oil has been filtered, particulates and contaminates may remain in the oil. In some scenarios, the filter may be clogged or even missing. To reduce negative effects (e.g., a disproportionate amount of contaminants in the sample chamber skewing the determined quality, failure of the sensor, clogging of the sample chamber or the oil filter system line in general) that may be caused by such contaminants, the single-sensor system may be designed such that the amount of contaminates collected by one or more of the sensor or the sample chamber is reduced. Moreover, the single-sensor system may be designed such that the sensor and the sample chamber encourage the flushing of contaminates from the sensor and the sample chamber.

In addition, because the sensor is located in the oil filter system line, the sensor may be exposed to over-pressure conditions resulting from faults in the oil filter system plumbing and components, such as, for example, when a deadhead occurs. A deadhead is a fault condition in which a pump outlet is blocked for some reason, such as, for example, when a return valve has failed closed. Persistent pressures of 400 to 600 PSI may develop in a fluid line during a deadhead. Consequently, the oil filter system, and, more specifically, the sensor and the sample chamber, may be designed to be durable no that such over-pressure conditions may not cause significant damage to the sensor.

Moreover, in existing in-vat sensor systems, the oil at the sensor electrode is essentially stationary; however, as disclosed herein, the sensor may be disposed in the oil filter system line, through which oil may flow. Consequently, the oil may move at a substantial velocity past the sensor, and this may change the magnitude of the current flow, and, accordingly, the apparent conductivity of the oil. Therefore, the system disclosed herein may be designed to perform one or more of pausing or stopping the oil flow through the sample chamber each time a conductivity measurement is made and compensating for the difference between the apparent conductivity and the actual conductivity of the oil based on the movement of the oil through the sample chamber.

Accordingly, the present disclosure may relate to, for example, a system and method with the cost and simplicity benefits of a single sensor, while overcoming the above-described and other disadvantages. Further, the present disclosure may relate to, for example, an oil quality measurement system and method that may measure the conductivity of the oil and may use the measured conductivity to infer the suitability of the oil for cooking (e.g., to determine a quality of the oil). Nevertheless, the present disclosure also may relate to quality measurement systems and methods that may measure properties other than conductivity, such as, for example, one or more of capacitance (e.g., total polar compounds), viscosity, and acidity, each of which also may be used to determine the oil quality. Moreover, the present disclosure may relate to cooking media or other media distinct from oil, such as, for example, one or more of water, lard, and shortening. White many of the principles of the present invention may apply to oil quality sensors of any type, certain features disclosed herein may be specifically related to measuring conductivity.

Embodiments of the present invention, and their features and advantages, may be understood by referring to FIGS. 1-6, like numerals being used for corresponding parts in the various drawings.

FIG. 1 shows a cooking medium system, such as a fryer system 100. Fryer system 100 may be configured for use in a gas or electric fryer system. Fryer system 100 may comprise at least one cooking vessel 101 (e.g., a frypot, a vat), which may be configured to hold and heat a cooking medium M (e.g., an oil, a liquid shortening, a meltable-solid shortening), as shown in FIG. 1. Although cooking vessel 101 may be suitable for an open-well fryer, fryer system 100 also may be used in a pressure fryer. Further, fryer system 100 may comprise a filter system 200. Cooking vessel 101 may comprise a drain valve 103, which may permit cooking medium M to drain from cooking vessel 101 into a filter container 201 (e.g., a filter pan) of filter system 200 when drain valve 103 is in an open position. When drain valve 103 is in a closed position, cooking vessel 101 may retain cooking medium M therein.

Filter system 200 may comprise filter container 201, a filter medium 203, a pump 205 filter pump), a process control 207 (e.g., a processor, a controller), a return valve 209, and a sample chamber 300. Filter medium 203 may be disposed within filter container 201, such that cooking medium M may flow through filter medium 203 when exiting filter container 201. Pump 205 may be disposed along a filter path AA between filter container 201 and return valve 209. As shown in FIG. 1, filter system 200 further may comprise fluid conduits 211, 213, and 215 (e.g., pipes, tubes, channels), which may fluidly connect one or more of filter container 201, pump 205, return valve 209, and sample chamber 300 along filter path AA. Process control 207 may selectively control pump 205 to energize (e.g., activate) and de-energize (e.g., de-activate, pause). When pump 205 is energized, pump 205 may convey cooking medium M along filter path AA from filter container 201, through filter medium 203, to return valve 209. Consequently, filter medium 203 may remove particulate material foodstuff and other contaminants) from cooking medium M before cooking medium M travels through pump 205 and, in certain configurations, before cooking medium M travels through sample chamber 300.

Return valve 209 may be fluidly connected to cooking vessel 101, such that pump 205 may drive cooking medium M through return valve 209 into cooking vessel 101 when return valve 209 is in an open position. When return valve 209 is in a closed position, fluid. communication between filter system 200 and cooking vessel 101 ma not occur. Consequently, process control 207 may control pump 205 to de-energize when return valve 209 is in the closed position in order to prevent a build-up of pressure (e.g., a deadhead) between pump 205 and return valve 209. In certain configurations, process control 207 may control one or more of drain valve 103 and return valve 209 to change between the open and closed positions thereof.

During a filter process (e.g., a cooking media filter process, an oil filter process), process control 207 may control drain valve 103 to change to the open position, and cooking medium M may drain from cooking vessel 101 to filter container 201. Subsequently, process control 207 may control return valve 209 to change to the open position, process control 207 may control filter pump 205 to energize, and filter pump 205 may circulate cooking medium M through filter medium 203 in filter container 201 back to cooking vessel 101. Consequently, filter medium 203 may collect particulates in cooking medium M, thus removing many of the particulates from cooking medium M.

Sample chamber 300, which is described in more detail below with reference to FIGS. 2A-2C, may comprise an electrode 301 and a temperature sensor 303 disposed therein. Further, sample chamber 300 also may comprise a level sensor 321 (described below) disposed therein, Electrode 301 may function as a sensor to measure a specified property of cooking medium M, which may be used to determine a quality of cooking medium M. In the exemplary configuration of FIG. 1, electrode 301 may measure, for example, a conductivity of cooking medium M. Nevertheless, electrode 301 or another specialized sensor (not depicted) may measure, for example, one or more of capacitance, acidity, and viscosity of cooking medium M, each of which may be used to determine the quality of cooking medium M. Electrode 301 may measure the conductivity of cooking medium M by, for example, applying an excitation voltage to cooking medium M and measuring the resultant potential difference. Temperature sensor 303 may measure a temperature of cooking medium M, which process control 207 may use to compensate for temperature differences between a cooking temperature of cooking medium cooking vessel 101 and a temperature of cooking medium M in sample chamber 300 when determining the quality of cooking medium M.

Process control 207 may control a timing at which electrode 301 may measure the conductivity and temperature of cooking medium M. As described in more detail below, process control 207 may control electrode 301 and temperature sensor 303 to perform respective measurements of the conductivity of cooking medium M and the temperature of cooking medium M during a filter process when enough cooking medium M is in sample chamber 300 to cover the active portions of electrode 301 and temperature sensor 303 (e.g., when electrode 301 and temperature sensor 303 are completely immersed in cooking medium M). By performing the respective measurements of conductivity and temperature when electrode 301 and temperature sensor 303 are completely immersed in cooking medium M, electrode 301 and temperature sensor 303 may more accurately measure the conductivity and the temperature of cooking medium M. In certain configurations, temperature sensor 303 may be omitted. In other configurations, electrode 301 and temperature sensor 303 may each measure the respective one of the conductivity and the temperature of cooking medium M at different timings or, for example, in scenarios when cooking medium M covers one of electrode 301 and temperature sensor 303 but not the other.

As depicted in FIG. 1, sample chamber 300 is disposed downstream of filter medium 203 along filter path AA, and sample chamber 300 is disposed upstream of pump 205 along filter path AA. Sample chamber 300 may be disposed downstream of filter medium 203, such that cooking medium M entering sample chamber 300 may already be filtered. Consequently, cooking medium M may have fewer particulates therein that may damage electrode 301 or block the inlets and outlets to sample chamber 300. Therefore, electrode 301 may be less likely to be damaged and conductivity measurements may be more accurate because there are fewer particulates in cooking medium M to bias the conductivity measurement. In certain configurations (not depicted), sample chamber 300 may be disposed downstream of pump 205 along filter path AA. Whether sample chamber 300 is upstream or downstream of pump 205 along filter path AA may not substantially affect the process of measuring conductivity or the measured conductivity of cooking medium M; however, components and seals (not shown) of sample chamber 300 may experience less stress when a deadhead occurs when sample chamber 300 is disposed upstream of pump 205. As described above, a deadhead is a fault condition in which an outlet of pump 205 is blocked for some reason, such as, for example, because return valve 209 has failed closed. Persistent pressures of 400 to 600 PSI may develop during a deadhead. When sample chamber 300 is disposed upstream of pump 205 along filter path AA (e.g., in a pump inlet line between filter container 201 and pump 205), sample chamber 300 and components thereof may not be exposed to these pressures.

Figure 2A:
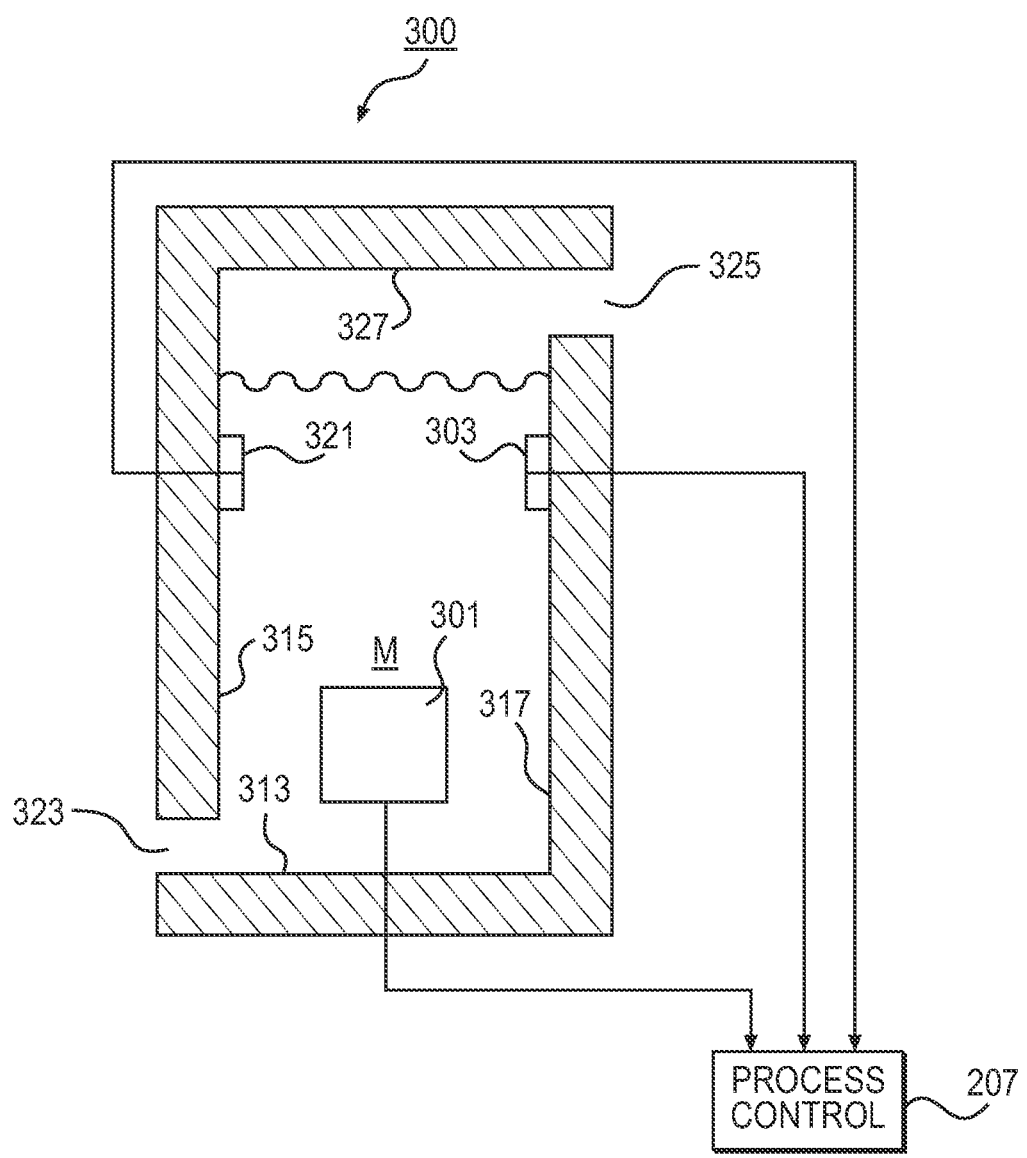
FIG. 2A is a schematic front view of a sample chamber.
Figure 2B:
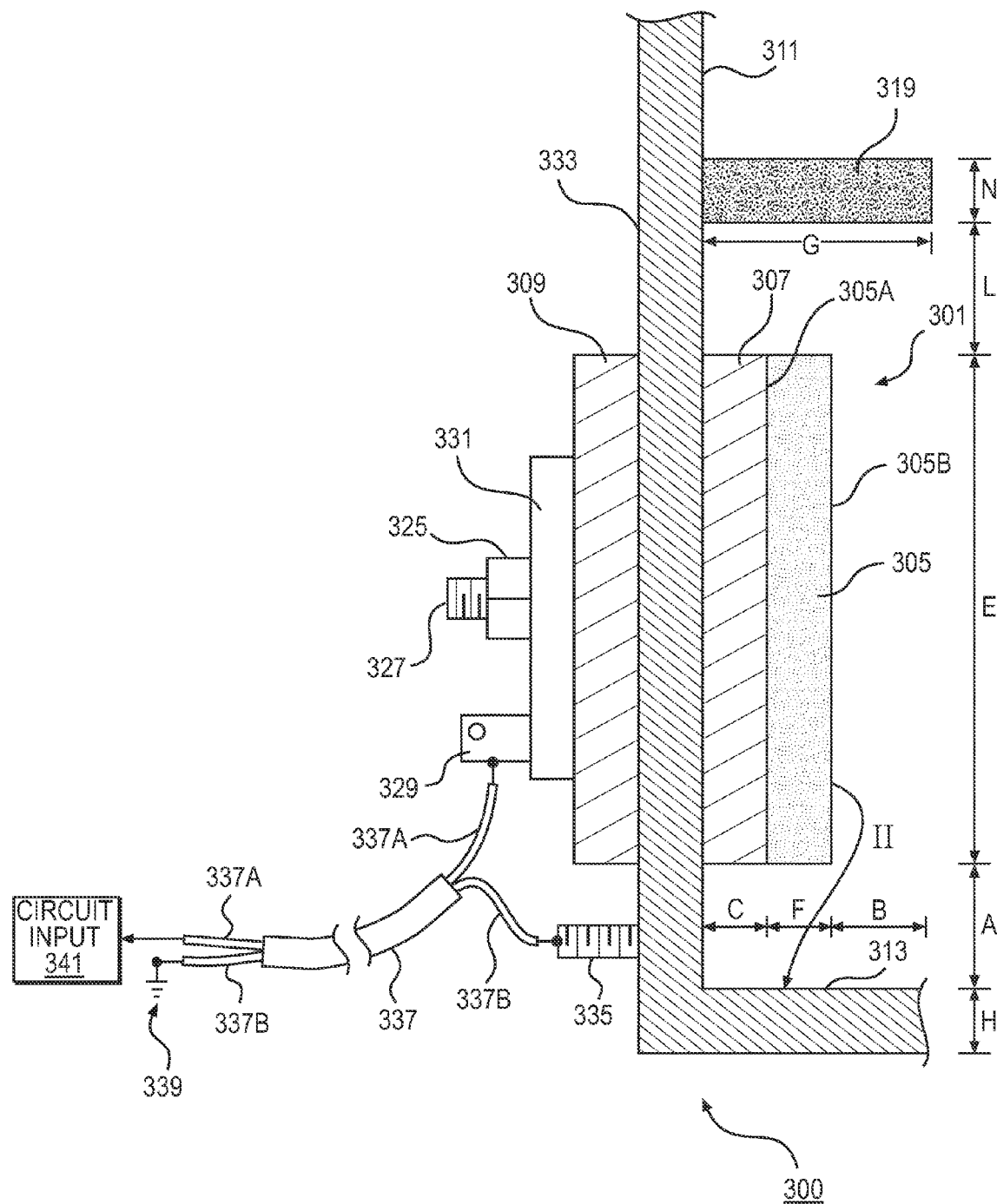
FIG. 2B is a partial schematic side view that shows an electrode mounted to the wall of the sample chamber of FIG. 2A.
Figure 2C:
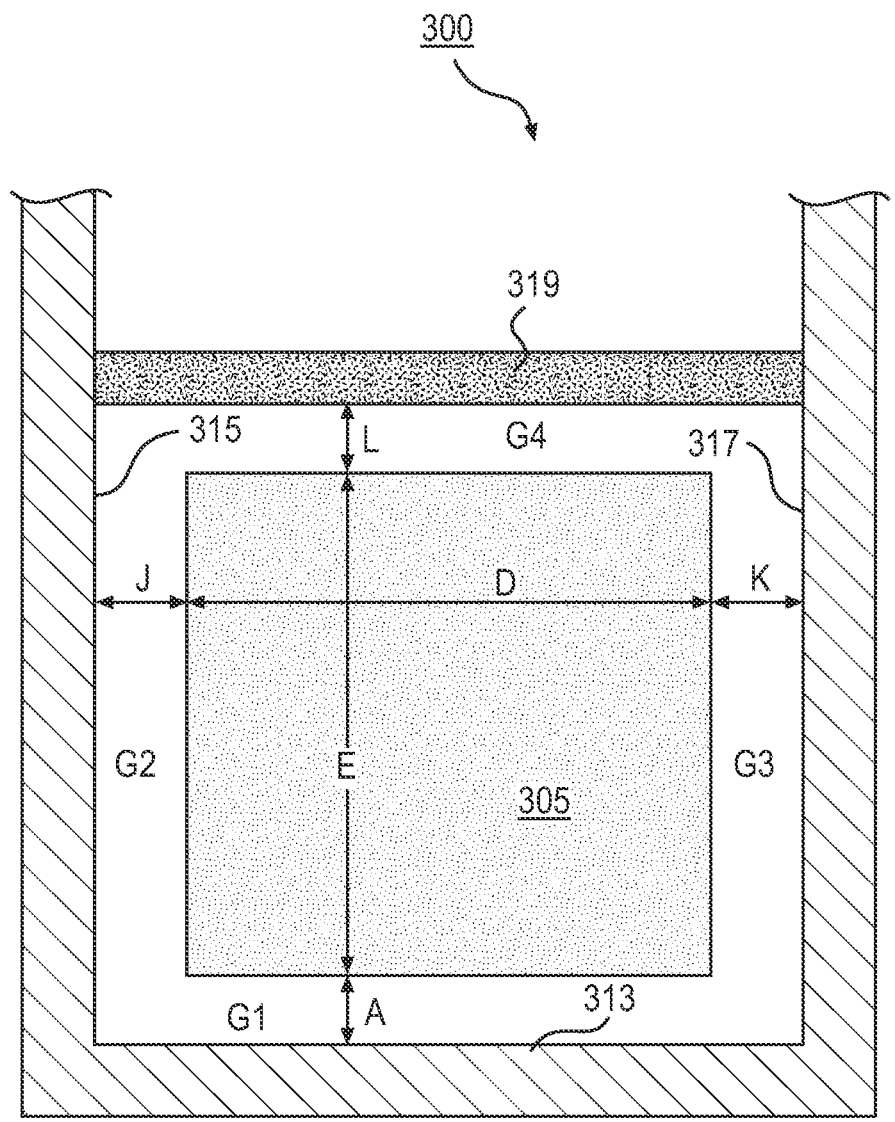
FIG. 2C is partial schematic front view that shows the electrode of FIG. 2B mounted to the wall of the sample chamber of FIG. 2A.

Referring now to FIGS. 2A-2C, configurations of sample chamber 300, electrode 301, and associated components now are described. FIG. 24 is an enlarged schematic front view of sample chamber 300. Sample chamber 300 may comprise a floor 313, which is disposed on an inner surface of a base of sample chamber 300, and a top 327 (e.g., ceiling), which is disposed on an inner op surface of sample chamber 300. Further, sample chamber 300 may comprise inner side walls 311, 315, and 317, as well as another side wall (not shown). As shown in FIG. 2A, sample chamber 300 may comprise a substantially parallelepiped shape. Nevertheless, the geometry of sample chamber 300 may take various forms depending on space constraints in fryer system 100. For example, in certain configurations, one or more of fluid conduits 211 and 215 may comprise piping or tubing that functions as a sample chamber similar to sample chamber 300. In certain configurations, such piping or tubing may be mounted vertically or at some angle above horizontal, such that cooking medium M may cover one or more of electrode 301 and temperature sensor 303 while the one or more of electrode 301 and temperature sensor 303 is measuring the respective specified property of cooking medium M. In certain configurations, such as the configurations shown in FIG. 6, a U-shaped trap 400 (described below) may be disposed in a pipe or a tube along filter path AA, may comprise one or more of electrode 301 and temperature sensor 303 disposed therein, and may function similarly to sample chamber 300.

Inner side wall 315 and floor 313 may form a lower opening 323 therebetween in sample chamber 300. Lower opening 323 may be disposed along filter path AA and may be fluidly connected to filter pan 201 through, for example, fluid conduit 211, and lower opening 323 may receive cooking medium M therefrom. Inner side wall 317, which may be opposite to inner side wall 315, and top 327 may form an upper opening 325 therebetween in sample chamber 300. Upper opening 325 may be disposed along filter path AA and may be fluidly connected to return valve 209 through, for example, fluid conduits 213 and 215, and upper opening 325 may discharge cooking medium M thereto. Consequently, cooking medium M may enter sample chamber 300 via lower opening 323 and may exit sample chamber 300 via upper opening 325. Although FIG. 2A depicts lower opening 323 and upper opening 325 on opposite sides of sample chamber 300, in certain configurations, lower opening 323 and upper opening 325 may be formed on a same side of sample chamber 300 or on adjacent sides of sample chamber 300. Further, in certain configurations, lower opening 323 and upper opening 325 may be formed at the same distance from floor 313 or from top 327. Moreover, in certain configurations, cooking medium M may enter sample chamber 300 via upper opening 325 and may exit sample chamber 300 via lower opening 323. Lower opening 323 is omitted from FIG. 2C for illustrative purposes.

In the configuration of FIG. 2A, electrode 301 may be disposed on inner side wall 311 (shown in FIG. 2B), and temperature sensor 303 may be disposed on inner side wall 317. In the configuration of FIG. 2A, electrode 301 and temperature sensor 303 may be disposed at different distances from floor 313 or top 327; however, in certain configurations, for example, electrode 301 and temperature sensor 303 may be disposed at the same distance from floor 313 or top 327, such that electrode 301 and temperature sensor 303 may become immersed in cooking medium M simultaneously. Further, in certain configurations, level sensor 321 may be disposed on inner side wall 315 at a distance from floor 313 or top 327 that is different or the same as the distance from one or more of electrode 301 and temperature sensor 303 to floor 313 or top 327. Nevertheless, in certain configurations, for example, one or more of electrode 301, temperature sensor 303, and level sensor 321 may be disposed on one or more of inner side wall 311, inner side wall 315, inner side wall 317, floor 313, and top 327. Electrode 301, temperature sensor 303, and level sensor 321 may be disposed closer to floor 313 than upper opening 325.

As cooking medium M is filtered, cooking medium M flows through sample chamber 300. Complete immersion of electrode 301 and temperature sensor 303 may occur as cooking medium M enters at the bottom of sample chamber 300 through lower opening 323, begins to fill sample chamber 300, and discharges at the top of sample chamber 300 through upper opening 325, which may be disposed closer to top 317 than electrode 301 and temperature sensor 303. A volume of sample chamber 300 may be as small as practical, consistent with mounting requirements for electrode 301 and temperature sensor 303, such that little or no cooking medium M may remain in sample chamber 300 after filtering is complete.

FIG. 2B is a partial schematic side view that shows electrode 301 mounted to the wall of sample chamber 300 of FIG. 2A. Electrode 301 may measure, for example, the conductivity of cooking medium M and may be similar to or the same as the electrode described in U.S. patent application Ser. No. 13/215,158. Nevertheless, U.S. patent application Ser. No. 13/215,158 discloses that the electrode may be disposed in the vat. Consequently, the electrode disclosed in U.S. patent application Ser. No. 13/215,158 may be exposed to physical damage from equipment operators during processes such as scraping during a vat cleaning procedure. U.S. patent application Ser. No. 13/215,158 discloses that a guard ring may protect the electrode from damage and dislocation. According to the present disclosure, electrode 301 may be disposed in filter system 200, rather than in cooking vessel 101. Thus, electrode 301 may be protected from damage by virtue of the remote location of electrode 301 in filter system 200. Consequently, a guard ring may not be necessary for protection of electrode 301.

U.S. patent application Ser. No. 13/215,158 discloses, however, that the guard ring serves an additional beneficial function of increasing the sensitivity of the conductivity measurement. Therefore, without the sensitivity-enhancing functionality of the guard ring, the sensitivity of the electrode may be too low to accurately measure conductivity or another desired property of a cooking medium.

Accordingly, guard ring-like functionality may be beneficial to the sensitivity of electrode 301 in the present disclosure. Such guard ring-like functionality may be accomplished without an actual guard ring by sizing sample chamber 300 to provide an appropriately-dimensioned gap between electrode plate 305, inner side walls 315 and 317 of sample chamber 300, and floor 313 of sample chamber 300. This arrangement may provide three guard ring-like surfaces, which may duplicate the sensitivity-enhancing functionality of the guard ring. A fourth guard ring-like surface may be provided, if desired or necessary, by disposing an additional conductor 319 (e.g., an additional conductive surface) above an electrode plate 305, as shown in FIGS. 2B and 2C. Conductor 319 is omitted from FIG. 2A for illustrative purposes.

Electrode 301 may be disposed in sample chamber 300 and may be mounted to inner side wall 311 of sample chamber 300, such that the portions of electrode 301 within sample chamber 300 may be completely immersed in cooking medium M. Electrode 301 may send a signal to a signal conditioning circuit (not shown), which may measure the signal from electrode 301 and send a signal to process control 207 for further processing (e.g., generating an alert when the conductivity of cooking medium M drops below a threshold level). The conductivity of cooking medium M may indicate the quality of cooking medium M, as described in more detail previously.

In particular, FIG. 2B shows a side view of electrode 301 when electrode 301 is mounted to inner side wall 311 of sample chamber 300. Similarly, FIG. 2C shows a front view of electrode 301. Electrode 300 may comprise electrode plate 305, which may comprise, for example, stainless steel or another suitable material. Electrode plate 305 may be polished on one side in order to create a smooth surface. In certain configurations, for example, electrode plate 305 may be fixed to sample chamber 300 by a flattened bolt 327. Consequently, electrode plate 305 may form a hole at least partially through a central portion thereof. In certain configurations, for example, electrode plate 305 may form the hole completely therethrough. Moreover, a portion of the hole may receive flattened bolt 327 therein, In certain configurations, for example, the portion of flattened bolt 327 that is inserted into the hole in electrode plate 305 may be unthreaded to provide a smooth surface at electrode plate 305, as well as to create a tight seal to reduce or prevent cooking medium leakage.

As shown in FIG. 2C, electrode plate 305 has a width D and a height E. As shown in FIG. 2B, electrode plate 305 has a thickness F. As described above, a larger electrode may produce a larger electrode gain, which may correspond to a signal of greater quality being generated by electrode 301. Nevertheless, space in sample chamber 300 may be limited in order to reduce an amount of cooking medium M trapped therein. Moreover, the electrode height E may be small enough, such that the electrode is completely immersed in cooking medium Ni rapidly during the filter process. Although other values may yield similar results, certain configurations disclosed herein may utilize a width D of electrode plate 305 of 2.000 inches (5.080 centimeters), a height E of 0.750 inches (1.905 centimeters), and a thickness F of 0.105 inches (0.2667 centimeters). These values may work particularly with the other values described in the present disclosure, particularly of the dimensions of the gap described herein. Other values of these dimensions may be appropriate, but these particular values may yield the unexpected result of a relatively high electrode gain with a relatively low electrode size.

As described above, a first side 305A of electrode plate 305 may face toward a center of sample chamber 300. A second side 305B of electrode plate 305, which may be opposite to first side 305A, may be pressed against an insulator 307 (e.g., a first insulator). Insulator 307 may be, for example, a molded body comprising polytetraflouroethylene ("PTFE"). Insulator 307 may form a hole therethrough, such that insulator 307 also may be threaded through flattened bolt 327. In certain configurations, for example, insulator 307 may comprise two separated silicon washers (not shown) to provide a tighter fit and to reduce or prevent cooking medium leakage through the hole in insulator 307. As shown in FIG. 2B, when installed, insulator 307 may be disposed between inner side wall 311 of sample chamber 300 and electrode plate 305, and insulator 307 may be aligned with electrode plate 305 in the width and height directions. Insulator 307 has a thickness C, which also may affect the electrode gain of electrode 301. Although incorporating a thinner insulator 307 into electrode 301 may increase the electrode gain, incorporating the thinner insulator 307 into electrode 301 also may increase the risk that suspended food particles may bridge electrode plate 305 and inner side wall 311. In certain configurations, for example, insulator 307 may have a thickness C of 0.0930 inches (0.2362 centimeters).

In certain configurations, for example, insulator 307 may have the same width and height as electrode plate 305 (e.g., width D and height E). When insulator 307 comprises a greater width or height than electrode plate 305, then the electrode gain may be low and may decrease rapidly as one or more of the width and height of insulator 307 increases. Moreover, when insulator 307 comprises a width or height less than electrode plate 305, then the electrode gain may be high; however, the risk of contamination may increase because suspended food particles may become trapped between inner side wall 311 and electrode plate 305.

As shown in FIGS. 2B and 2C, electrode 301 may be disposed on inner side wall 311 such that a gap G1 of distance A is formed between floor 313 and a wall of electrode plate 305, a gap G2 of distance J is formed between inner side wall 315 and another wall of electrode plate 305, and a gap G3 of distance K is formed between inner side wall 317 and still another wall of electrode plate 305. Distances A, J, and K also may affect the electrode gain of electrode 301. In certain configurations, for example, one or more of distances A, J, and K may be 0.167 inches (0.424 centimeters). In addition, additional conductor 319 may be disposed above electrode plate 305 such that a gap G4 of distance L is formed between additional conductor 319 and yet another wall of electrode plate 305, as shown in FIGS. 2B and 2C. Distance L also may affect the electrode gain of electrode 301 and may also be 0.167 inches (0.424 centimeters). In certain configurations, however, one or more of distances A, J, K, and L may be different from others of distances A, J, K, and L. A smaller gap G1, G2, G3, or G4 may increase the electrode gain; however, a smaller gap G1, G2, G3, or G4 also may expose the electrode 301 to suspended food particles, which may collect in one or more of the gaps G1, G2, G3, and G4, and which may decrease the accuracy of electrode 301. In certain configurations, the size of one or more of gaps G1 through G4 may be selected based on one or more of the height E, width D, and thickness F of electrode plate 305.

As shown in FIG. 2B, the base of sample chamber 300, on which floor 313 is disposed, may comprise a thickness H, and additional conductor 319 may comprise a thickness N. Thickness H of the base of sample chamber 300, as well as the thickness of the walls of sample chamber 300, and thickness N of additional conductor 319 may affect the electrode gain of electrode 301; however this effect on electrode gain may be less significant than the effect on electrode gain attributed to the above-described dimensions, In certain configurations, for example, one or more of thicknesses H and N may be within a range of 0.075 inches to 0.083 inches (0.191 centimeters to 0.211 centimeters). Similarly, additional conductor 319 may extend outward from inner side wall 311 for a distance G as shown in FIG. 2B. Additional conductor 319 may be designed to have a distance G based on the thickness F of electrode plate 305 and insulator 307, as well as based on the desired electrode offset for increasing electrode gain. In certain configurations, for example, the distance G may be 0.250 inches (0.6350 centimeters). Referring again to FIG. 2B, insulator 307 and electrode plate 305 may be offset below the edge of additional conductor 319 to provide protection from damage and abuse. In FIG. 2A, the distance B may be the difference between distance G and the sum of thicknesses C and F. In certain configurations, distance B may be 0.057 inches (0.145 centimeters). In other configurations, distance B may be zero because it truly not be necessary to provide for such robust protection of electrode plate 305 within sample chamber 300.

Insulator 307, electrode plate 305, and additional conductor 319 may be positioned on an inner side wall 311 of sample chamber 300, as shown in FIGS. 2B. In certain configurations, for example, insulator 307, electrode plate 305, and inner side wall 311 may form holes in respective central portions thereof, such that flattened bolt 327 may pass between them and fix electrode plate 305 and insulator 307 to inner side wall 311. Nevertheless, as shown in FIG. 2B, back insulator 309 may be positioned adjacent to an outer side wall 333 of sample chamber 300 opposite to inner the side wall 311, which contacts insulator 307. Back insulator 309 may comprise PTFE and may reduce or prevent leakage of cooking medium through the hole formed in inner side wall 311. In certain configurations, for example, back insulator 309 also may form a hole therethrough, through which flattened bolt 327 also may pass.

A seal washer (not shown) also may be positioned behind inner side wall 311. The seal washer may contact back insulator 309 and may compress back insulator 309 against outer side wall 333 to create a tight seal and reduce or prevent leakage of cooking medium through the hole formed in inner side wall 311. The seal washer 331 may comprise stainless steel or another suitable material.

As shown in FIG. 2B, an electrode contact comprising a base plate 331 and a terminal 329 may be positioned on the opposite side of inner side wall 311 from electrode 301. In certain configurations, for example, the electrode contact may comprise base plate 331 and two terminals 329 (the second terminal 329 is omitted from FIG. 2B for illustrative purposes) positioned on each side of the electrode contact, as shown in FIG. 2B. Although the electrode contact may comprise two terminals 329, one terminal 329 may connected to a signal conditioning circuit (not shown), and the other terminal 329 may balance the electrode contact, but may not necessarily be connected to the signal conditioning circuit. Either of the two terminals 329 may be used to connect the electrode contact to the signal conditioning circuit. The electrode contact may be electrically connected to electrode plate 305.

As shown in FIG. 2B, a nut 325 may be placed on an outside end of flattened bolt 327, to secure the electrode contact, the seal washer, and back insulator 309 on outer side wall 333 and to secure insulator 307 and electrode plate 305 on inner side wall 311. Nut 325, which may comprise stainless steel or another suitable material, may ensure that there is a conduction path (e.g., via flattened bolt 327) between a terminal 329 of the electrode contact and electrode plate 305. Thus, flattened bolt 327, nut 325, base plate 331, terminals 329, and electrode plate 305 may be electrically connected with one another. Further, insulators 307 and 309 may insulate flattened bolt 327, nut 325, base plate 331, terminals 329, and electrode plate 305 from inner side wall 311 and outer side wall 333. Moreover, a ground stud 335 may be secured (e.g., welded) to sample chamber 300 at outer side wall 333.

An electrode cable 337 may comprise a first conductor 337A and a second conductor 337B. First conductor 337A may connect with terminal 329 and a circuit input 341 to establish an electrical connection therebetween. Second conductor 337B may connect with ground stud 335 and a circuit ground 339 to establish an electrical connection therebetween. Process control 207 may be connected with circuit input 341 and may apply an excitation voltage (e.g., a direct current voltage) at circuit input 341, A current generated by the excitation voltage may flow along first conductor 337A to terminal 329. The current may flow through base plate 331, through nut 325, through flattened bolt 327, and to electrode plate 305. Subsequently, when cooking medium M contacts both sample chamber 300 and electrode plate 305, the current may flow through cooking medium M along a current path, such as, for example, current path II shown by the arrow in FIG. 2B, to sample chamber 300 (e.g., at one or more of inner side walls 311, 315, and 317, floor 313, and additional conductor 319) and through ground stud 335 to second conductor 337B. Thereafter, the current may flow through second conductor 337B to a circuit ground 339. Circuit ground 339 may be a ground connection for process control 207, such that a complete electrical circuit may be formed between electrode 301, process control 207, and ground stud 335 when cooking medium M is in contact with electrode 301 and sample chamber 300. Consequently, cooking medium M may function as a conductive path between electrode 301 and ground stud 335, even when a direct electric connection between electrode 301 and ground stud 335 may not exist because of insulators 307 and 309. Connecting an electrical circuit to circuit ground 339 through ground stud 335 near terminal 329, as described above and as depicted in FIG. 2B, may reduce electrical noise in the electrical circuit. In certain configurations, process control 207 may perform the signal conditioning processes disclosed in U.S. patent application Ser. No. 13/215,158.

A filter process in which process control 207 may utilize electrode 301 and temperature sensor 303 to monitor a quality of cooking medium M now is described with reference to FIG. 3. The filter process may comprise three distinct phases: a drain phase, a wash phase, and a fill phase.

Figure 4:
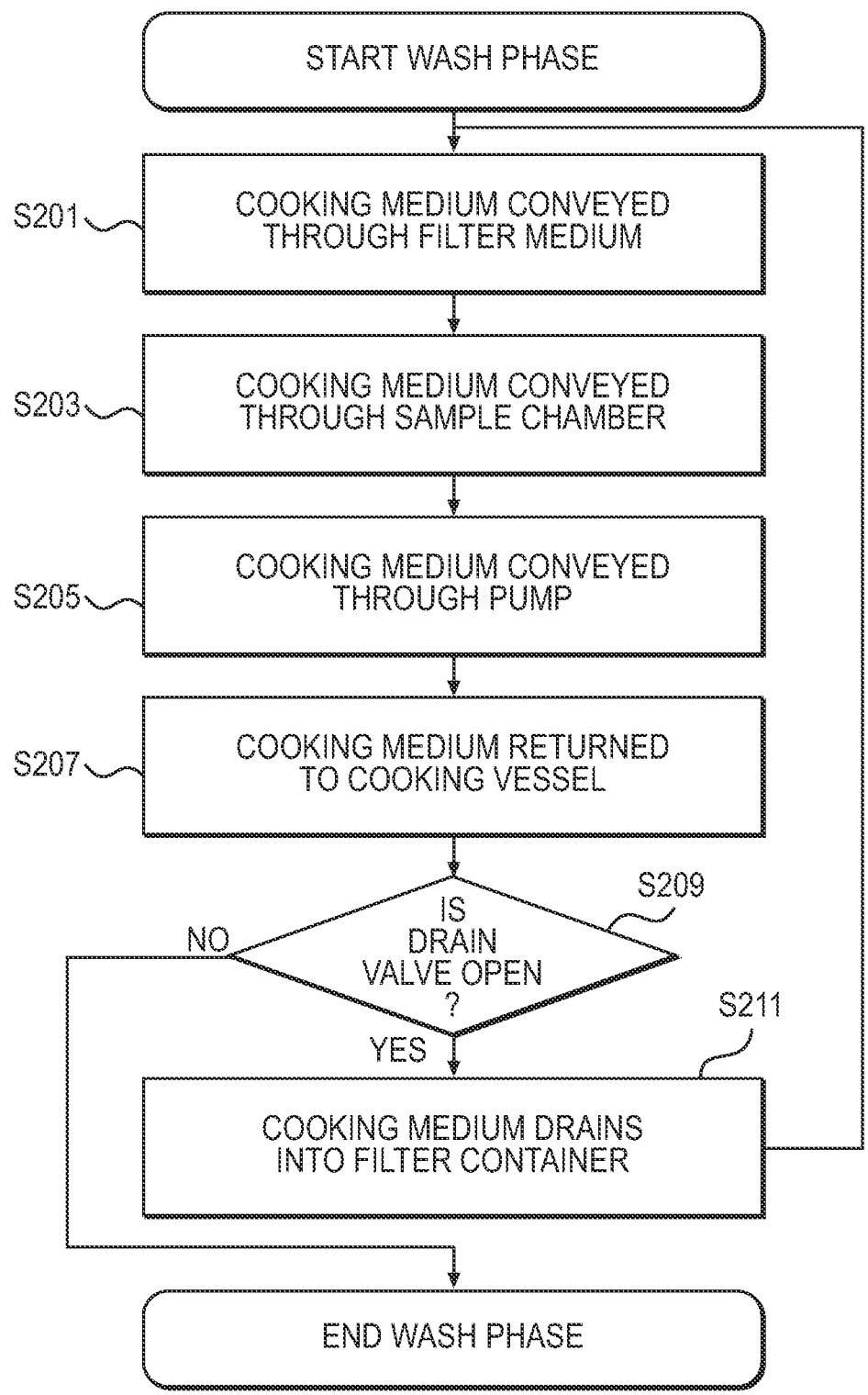
FIG. 4 is a flow sheet that shows a wash phase of the filter process of FIG. 3.

During the drain phase, process control 207 may control drain valve 103 to open (step S101), and cooking medium M may drain from cooking vessel 101 into filter vessel 201 (step S103). During the wash phase, drain valve 103 may remain open, process control 207 may control return valve 209 to open (step S105), and process control 207 may energize (e.g., activate) pump 205 to start conveying cooking medium M along filter path AA (step S107). This may cause cooking medium M to circulate through filter medium 203 and back into cooking vessel 101, as shown in FIG. 4. In particular, after process control 207 initiates the wash phase, energized pump 205 may generate a pressure gradient within filter system 300 that may convey cooking medium M from filter container 201 through filter medium 203 (step S201), such that particulates and sediments may be removed from cooking medium M. Energized pump 205 subsequently may convey cooking medium M along filter path AA through sample chamber 300 (step S203). Thereafter, energized pump 205 may convey cooking medium M through a fluid passage in pump 205 (step S205) and into fluid conduit 215. Subsequently, pump 205 may return cooking medium M to cooking vessel 101 (step S207). When drain valve 209 remains open after pump 205 returns cooking medium M to cooking vessel 101 (step S209: YES), cooking medium M may continue draining out of cooking vessel 101 and into filter container 101 (step S211), and the wash phase may continue by returning to step S201. Nevertheless, when drain valve 209 is closed, pump 205 may return cooking medium M to cooking vessel 101 (step S209: NO), the wash phase may end. Accordingly, the above-described phase may be called the "wash" phase because the circulation of cooking medium M may flush particulates and sediment from cooking vessel 101 into filter vessel 201, thus washing cooking vessel 101 and cooking medium M.

Figure 3:
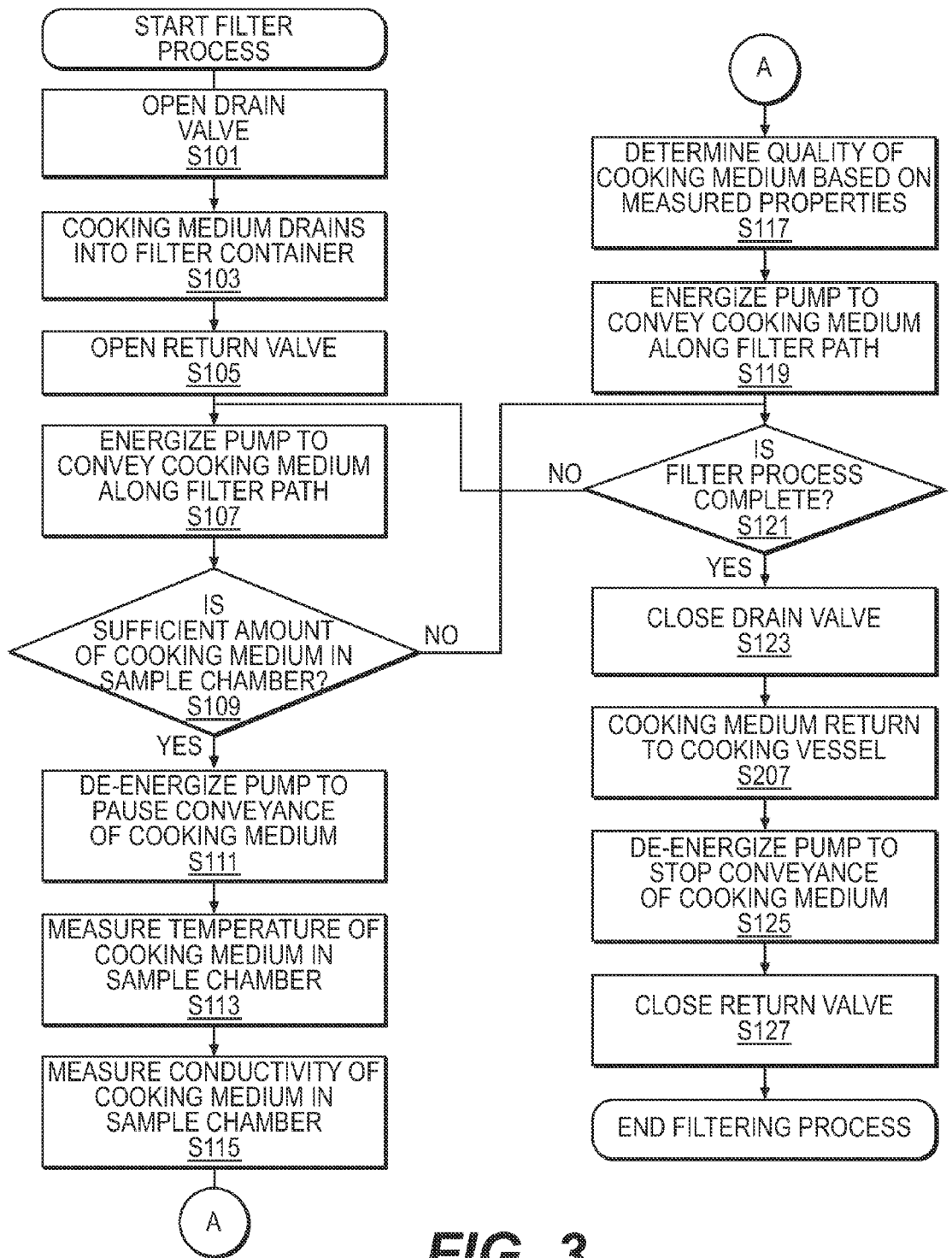
FIG. 3 is a flow sheet that shows a filter process performed by the filter system of FIG. 1, the filter process comprising an oil quality determining process.

The fill phase may begin when process control 207 controls drain valve 103 to close (step S123), as shown in FIG. 3. While return valve 209 still remains open, pump 205 may remain energized, and cooking medium M remaining in filter system 200 may be returned to cooking vessel 101 (step S207), After process control 207 detects that a sufficient amount of cooking medium M has been removed from filter system 300 (e.g., via level sensor 321, via pressure transducer 217, via, other means, such as determining that filter container 201 is evacuated), process control 207 may de-energize deactivate, pause) pump 205 to stop conveyance of cooking medium M throughout filter system 200 (step S125) and may control return valve 209 to close. Steps S125 and S127 may be performed simultaneously or closely in time, such that cooking medium M may not drain back into filter system 200 via, return valve 209, and such that a deadhead may not occur. Thereafter, the fill phase may terminate. The above-described filter process may be performed as desired to maintain an efficient and sanitary fryer system 100. Further, in certain configurations, the above-described filter may be performed as often as desired to determine the quality of cooking medium M (described in more detail below).

While process control 207 may control electrode 301 and temperature sensor 303 to measure the conductivity and temperature of cooking medium M at any time during the filter process, measuring the conductivity and temperature of cooking medium M under certain conditions may improve the accuracy of the measurements. For example, in certain configurations, process control 207 may control electrode 301 and temperature sensor 303 to measure the conductivity and temperature of cooking medium M after determining (e.g., via level sensor 321, via pressure transducer 217, via predetermined timing conditions, via other means) that electrode 301 and temperature sensor 303 are immersed in cooking medium M. Nevertheless, inaccuracies may still exist in the measurements of the specified properties due to other physical phenomena.

If electrode 301 was disposed in cooking vessel 101, cooking medium M around electrode 101 would be essentially stationary, and an excitation voltage across one or more of electrode plate 305 and additional conductor 319 may develop a static electric field. Nevertheless, when electrode 301 is disposed in flowing cooking medium M, as is the case when electrode 301 is disposed in sample chamber 300 along filter path AA during the filter process, the motion of cooking medium M may change an intensity of the electric field, which may further alter the current flow and lead to measurement errors. Further, the flow velocity of cooking medium M may be unpredictable because of variations in pump efficacy, filter flow resistance, and plumbing losses. Thus, momentarily stopping the flow of cooking medium M may eliminate such errors associated with flow variation. Therefore, in certain configurations, process control 207 may briefly de-energize pump 205 during the filter process, which may briefly stop (e.g., pause, retard) circulation of cooking medium M in filter system 200, when process control 207 controls one or more of electrode 301 and temperature sensor 303 to measure the respective one or more of the conductivity and temperature of cooking medium M. Such a stoppage or pause during the filter process may be referred to as an "acquisition pause" because the flow of cooking medium M may be paused to acquire the one or more of the conductivity and temperature measurements.

The acquisition pause may he as short as possible, such that a total fitter time may be short and fryer system 100 may keep up with product requirements during periods of increased customer demand. In certain configurations, the minimum period of time required for an acquisition pause, such that electrode 301 may acquire an accurate measurement, may be, for example, 30 seconds. Nevertheless, in other configurations, the minimum period of time required for an acquisition pause may be greater than or less than 30 seconds. Further, there may be particular points during the filter process when the acquisition pause may be more advantageous due to less increase in total filter time and improved measurement accuracy. For example, each of electrode 301 and temperature sensor 303 may have improved measurement accuracy when each of electrode 301 and temperature sensor 303 is immersed in cooking medium M. Thus, it may be beneficial to initiate the acquisition pause after there has been sufficient time and flow for cooking medium M to fill sample chamber 300 to a level at the top of or above electrode 301 and temperature sensor 303. Consequently, it may be beneficial to initiate the acquisition pause at the end of the wash phase when cooking medium M has filled sample chamber 300 to a level at the top of or above electrode 301 and temperature sensor 303. Further, at the end of the wash phase, the cooking medium M may he thoroughly mixed, so a homogenous sample may be available. In addition, at the end of the wash phase, the rate of cooling may have stowed, which may reduce response time errors from the temperature sensor, and which ma consequently reduce a temperature compensation error (described below). By the end of the wash segment, the flow may reach a steady state defined partially by a condition of filter medium 203 (e.g., whether filter medium 203 is a new filter or an extremely clogged filter).

Returning to FIG. 3, the acquisition pause now is described. Subsequent to process control 207 energizing pump 205 in step S107 and during the wash phase, process control 207 may determine whether a sufficient amount of cooking medium M exists in sample chamber 300 (step S109). In certain configurations, process control 207 may utilize one or more of level sensor 321, pressure transducer 217, predetermined timing conditions an amount of time required to fill sample chamber 300 based on a particular flow rate), and other means to make the determination of step S109. When process control 207 determines that a sufficient amount of cooking medium M does not exist in sample chamber 300 (step S109: NO), process control 207 may proceed to step S121 (described below). When process control 207 determines that a sufficient amount of cooking medium M exists in sample chamber 300 (step S109: YES), process control 207 may initiate an acquisition pause by de-energizing or reversing pump 205 to pause or retard conveyance of cooking medium M throughout filter system 200 (step S111).

Subsequently, during the acquisition pause, process control 207 may control temperature sensor 303 to measure a temperature of cooking medium M in sample chamber 300 (step S113). Further, during the acquisition pause, process control 207 may control electrode 301 to measure a conductivity or other property of cooking medium M in sample chamber 300 (step S115), In certain configurations, steps S113 and S115 may be performed simultaneously, such that the measured conductivity or other property may be accurately adjusted based on the measured temperature (described in detail below). In other configurations, each of steps S113 and S115 may be performed at different timings, which may be in a same or different order than that depicted in FIG. 3. Further, in other configurations, in lieu of or in addition to step S115, electrode 301 or another sensor may measure a property of cooking medium M that is different from conductivity, such as, for example, one or more of capacitance, viscosity, and acidity.

Subsequent to steps S113 and S115, process control 207 may determine a quality of cooking medium M based on one or more of the properties measured in one or more of steps S113 and S115 (step S117). In certain configurations, such as those shown in FIGS. 1-3, for example, in step S117, process control 207 may determine the quality of cooking medium M based on the measured conductivity and temperature of cooking medium M. In other configurations, for example, such as in a filter system that monitors capacitance, process control 207 may determine the quality of cooking medium M based on the measured capacitance of cooking medium M. Process control 207 may perform step S117 immediately after measuring properties in steps S113 and S115 or at a later point in the filter process after other steps have been performed. In some configurations, for example, process control 207 may wait to determine the quality of cooking medium M until after a plurality of measurements have been made during a plurality of filter processes. In other configurations, for example, process control 207 may wait to determine the quality of cooking medium M until after the fill phase ends (e.g., the filter process ends).

In certain configurations, it may be beneficial to measure the temperature of cooking medium M in addition to the conductivity of cooking medium M because the conductivity of cooking medium M may be substantially affected by the temperature of cooking medium M in addition to the quality of cooking medium M. Further, the temperature of cooking medium M may decrease during circulation through filter system 200 because filter container 201, sample chamber 300, and fluid conduits 211, 213, and 215 may each be colder than cooking medium M after it is discharged from cooking vessel 101. Consequently, it may be beneficial to adjust the measured conductivity of cooking medium M based on the measured temperature of cooking medium M and, subsequently, determine the quality of cooking medium M at a particular temperature, such as, for example, an average cooking temperature or a desired cooking temperature to which cooking medium M may be heated during operation of fryer system 100. Various methods known in the art may be used to compensate the oil quality measurement for temperature variations.

Figure 5:
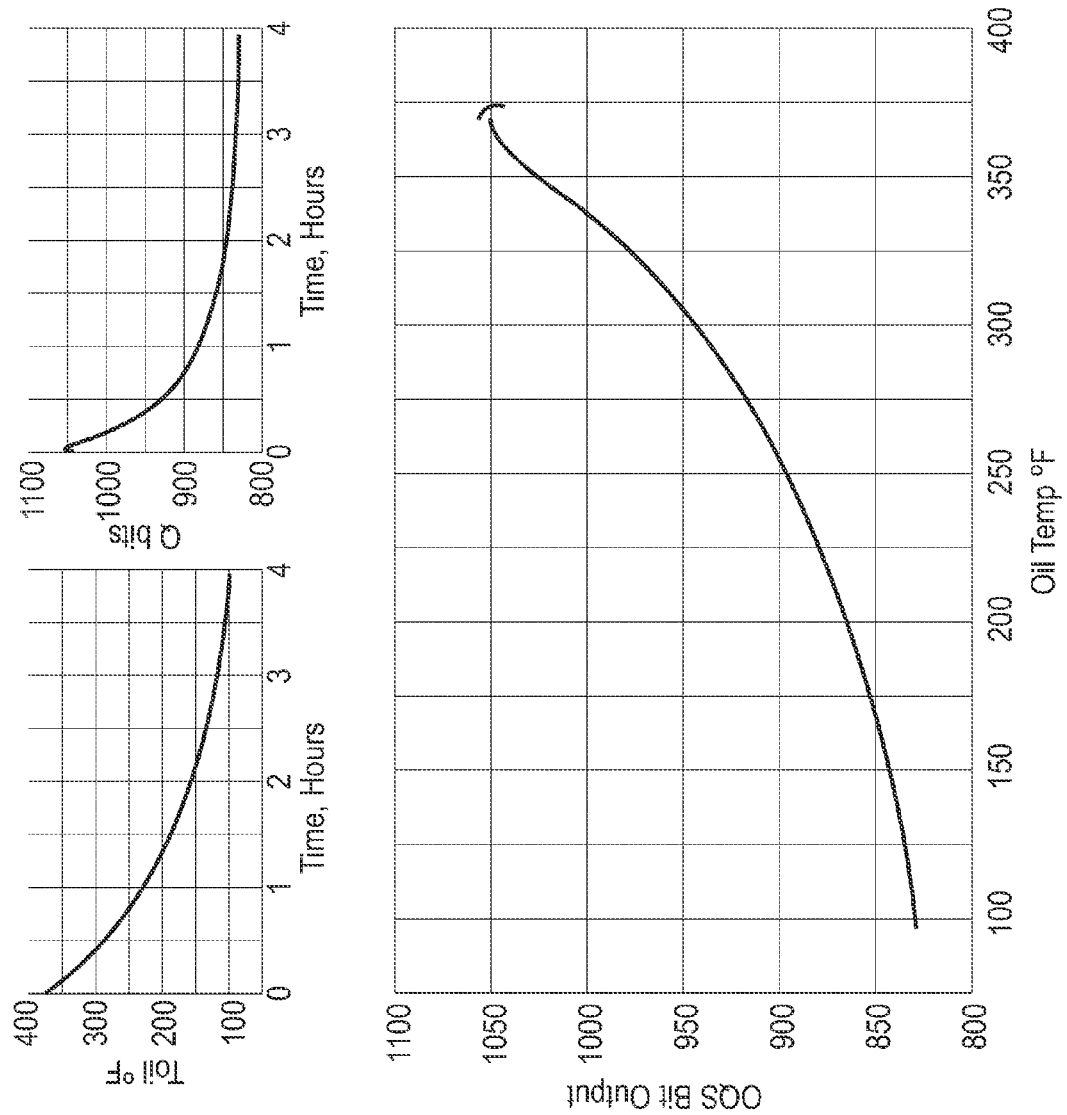
FIG. 5 is a graph that shows the effect of the temperature of the cooking medium on the measured conductivity of the cooking medium.
Figure 6:
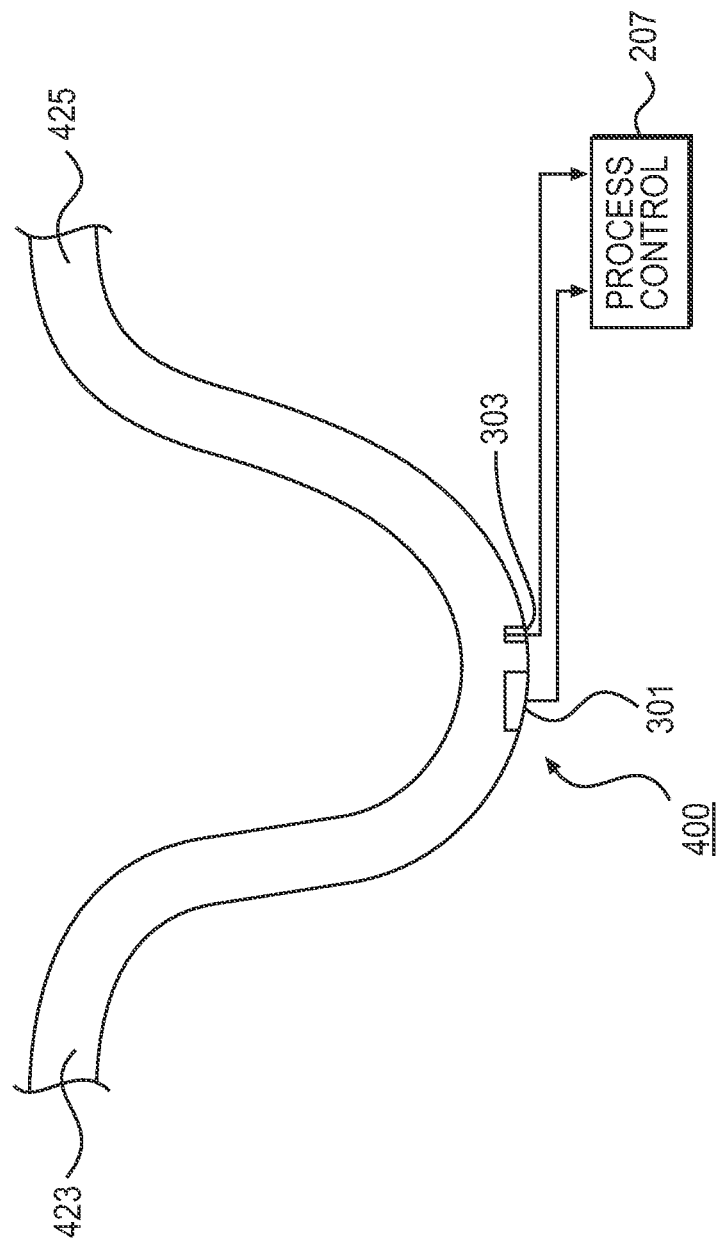
FIG. 6 is a schematic front view of a U-shaped sample chamber according to another configuration.

FIG. 5 shows experimental results for a particular oil sample that illustrate the effect of the temperature of cooking medium M on the measured conductivity of cooking medium M. The small plot at the top-left position in FIG. 5 shows the measured temperature of the oil sample in degrees Fahrenheit (identified as "Toil ° F." on the vertical axis) as a function of time in hours (identified as "Time, hours" on the horizontal axis). The small plot at the top-right position in FIG. 5 shows the quality conductivity measurement $_Q$ in units of bits (identified as "Q bits" on the vertical axis) as a function of time in hours (identified as "Time, hours" on the horizontal axis). The large plot at the bottom of FIG. 5 combines the above-described small plots together and shows the quality conductivity measurement for the oil sample in units of bits (identified as "OQS Bit Output" on the vertical axis) as a function of the oil temperature in degrees Fahrenheit (identified as "Oil Temp ° F." on the horizontal axis), If Q was independent of temperature, then the plot would be a straight, horizontal line. Instead, Q varies in a non-linear way with respect to temperature. Thus, temperature compensation may improve the accuracy and utility of the quality determined for cooking medium M.

Returning to FIG. 3, subsequent to measuring the specified properties in steps S113 and S115 and, in certain configurations, determining the quality of cooking medium M in S117, process control 207 may determine whether filter process S121 is complete (step S121). When process control 207 determines that filter process S121 is complete (step S121: YES), process control 207 may move to step S123 (described above). When process control 207 determines that filter process S121 is not complete (step S121: NO), process control 207 may return to step S107 (described above) and repeat steps S107, S109, and S121 (e.g., perform the wash phase) until process control 207 determines that filter process S121 is complete (step S121: YES) or process control 207 determines that a sufficient amount of cooking medium M exists in sample chamber 300 (step S109: YES).

In other configurations, for example, step S109 may be omitted and process control 207 may proceed to step S111 at a predetermined timing prior to the end of the wash phase, in some of such other configurations, process control 207 may control electrode 301 and temperature sensor 303 to perform a plurality of measurements at predetermined timings prior to the end of the wash phase, such that process control 207 may collect a plurality of data points, which may be statistically analyzed. In still other configurations, for example, temperature sensor 303 may measure the temperature of cooking medium M continuously during the fitter process.

In certain configurations, alternative means may be utilized to promote coverage of electrode 301 by cooking medium M. For example, a configuration such as that shown in FIG. 6, may be used in place of or in addition to sample chamber 300. As that shown in FIG. 6, a U-shaped trap 400 may be disposed in a pipe or a tube along filter path AA. One or more of electrode 301 and temperature sensor 303 may be disposed within a central portion of U-shaped trap 400, and U-shaped trap 400 may function similarly to sample chamber 300. U-shaped trap 400 may have an inlet opening 423 and an outlet opening 425 through which cooking medium M may enter and exit U-shaped trap 400. In certain configurations, inlet opening 423 and outlet opening 425 may be disposed at a same level. In other configurations, inlet opening 423 and outlet opening 425 may be disposed at different levels. As cooking medium M enters U-shaped trap 400 through inlet opening 423, gravity may cause cooking medium to congregate in the central portion of U-shaped trap 400 where the one or more of electrode 301 and temperature sensor 303 may be disposed. Consequently, the central portion of U-shaped trap 400 may fill with cooking medium M early in the filter process and electrode 301 and temperature sensor 303 may be covered with cooking medium M rapidly. Further, the central portion of U-shaped trap 400 may remain full of cooking medium during an acquisition pause (e.g., steps S111 through S117) because gravity may continue to urge cooking medium M into the central portion of U-shaped trap 400. Consequently, an accurate determination of the temperature, the conductivity, and other properties may be made by electrode 301 and temperature sensor 303 disposed in the central portion of U-shaped trap 400 during the acquisition pause.

In certain filter systems, it may be difficult to ensure that an electrode, such as electrode 301, is covered with cooking medium M. Such problems may occur when a flow rate of cooking medium through a filter system, such as filter system 200, may be intermittent and cooking medium M may comprise air bubbles therein. Therefore, in certain configurations disclosed herein, a level sensor 321 may be disposed on one or more of inner side walls 311, 315, and 317 of sample chamber 300, as depicted in FIGS. 1 and 2A, or in another portion of filter system 200. In such configurations, level sensor 321 may notify process control 207 when cooking medium M has reached or will reach a sufficient level in sample chamber 300 to cover one or more of electrode 301 and temperature sensor 303, and process control 207 subsequently may control the one or more of electrode 301 and temperature sensor 303 to begin measuring the specified properties of cooking medium M.

In certain configurations, electrode 301 may be the same as or similar to one or more of the electrodes disclosed in U.S. patent application Ser. No. 13/215,158. Further, in certain configurations filter system 200 may utilize one or more of the cooking medium quality monitoring processes and the cooking medium quality threshold detection processes disclosed in International Patent Application No. PCT/US2012/054231. Moreover, filter system 200 may comprise other components and perform other processes similar to or the same as those disclosed in one or more U.S. patent application Ser. No. 13/215,158 and International Patent Application No. PCT/US2012/054231. In addition, while a fryer system comprising a single conductivity sensor disposed in a filter system line may be described above, the invention is not limited to a single sensor system, and one or more conductivity sensors (e.g., electrodes), as well as one or more sample chambers and one or more temperature sensors, may be disposed in the fryer system described above (e.g., in the filter system line, in the cooking vessel, elsewhere in the fryer system).

In certain configurations, for example, the geometry of electrode 301 may be changed. For example, in particular configurations, electrode 301 may be smaller. In some configurations, for example, electrode 301 may be circular rather than rectangular. Further, while the mounting disposition of electrode 301 described above may provide certain performance advantages, other mounting dispositions may be utilized. For example, in certain configurations, one or more of electrode 301 and temperature sensor 303 may be disposed in filter container 201. In other configurations, for example, one or more of electrode 301 and temperature sensor 303 may be disposed at an outlet of pump 205. In still other configurations, for example, one or more of a plurality of electrodes 301 and a plurality of temperature sensors 303 may be disposed throughout filter system 200, such that a great amount of data may be collected and averaged to make amore accurate determination of the quality of cooking medium M.

In certain configurations, filter system 200 may comprise a pressure transducer 217, which may be disposed in filter path AA between pump 205 and return valve 209. In particular configurations, pressure transducer 217 may be disposed at an outlet of pump 205, as shown in FIG. 1. Pressure transducer 217 may generate a signal indicating a change in pressure when filter container 201 is evacuated, which may indicate that a filter process has ended. In certain configurations, the signal from pressure transducer 217 may be received by process control 207, such that process control 207 may confirm that an adequate amount of cooking medium M has flowed into and filled sample chamber 300, that cooking medium M has completely immersed one or more of electrode 301 and temperature sensor 303, and that conditions remain adequate to acquire an accurate measurement of the specified property (e.g., conductivity, capacitance, acidity, viscocity) while measuring the specified property.

In certain configurations, for example, a plurality of cooking vessels 101 may be attached to filter system 200, such that only one filter system 200 and one electrode 301 is necessary to wash and determine the quality of cooking medium M from each cooking vessel 101. Consequently, the high cost of purchasing and maintaining more than one filter system 200 and more than one electrode 301 may be avoided.

While the invention has been described in connection with various exemplary structures and illustrative embodiments, it will be understood by those skilled in the art that other variations and modifications of the structures, configurations, and embodiments described above may be made without departing from the scope of the invention. For example, this application comprises possible combinations of the various elements and features disclosed and incorporated by reference herein, and the particular elements and features presented in the claims and disclosed and incorporated by reference above may be combined with each other in other ways within the scope of the application, such that the application should be recognized as also directed to other embodiments comprising other possible combinations. Other structures, configurations, and embodiments consistent with the scope of the claimed invention will be apparent to those skilled in the art from a consideration of the specification or practice of the invention disclosed herein. It is intended that the specification and the described examples are illustrative with the true scope of the invention being defined by the following claims.

What is claimed is:

1. A cooking medium filter system configured to determine a quality of a cooking medium, the cooking medium filter system comprising:
   a filter container configured to receive the cooking medium from a cooking vessel;
   a filter medium disposed in the filter container and configured to remove contaminants from the cooking medium received in the filter container;
   a pump configured to convey the cooking medium along a filter path from the filter container to the cooking vessel;
   a sample chamber disposed in the filter path downstream from the filter medium, the sample chamber comprising an electrode disposed therein, and the sample chamber configured to receive therein a first quantity of the cooking medium that is sufficient to immerse the electrode therein; and
   a controller configured to control operations of the pump and configured to control the electrode to measure a property of the cooking medium that is associated with the quality of the cooking medium,
   wherein the electrode comprises:
      an electrode plate comprising a first side and a second side opposite the first side, the electrode plate configured to be immersed in the first quantity of cooking medium, the electrode plate having a height, a width, and a thickness; and
      an insulator formed on the first side of the electrode plate and covering a surface of the electrode defined by the height and the width,
   wherein the insulator is fixed to a first inner side wall of the sample chamber,
   wherein the electrode is disposed within the sample chamber to form a first gap between a floor of the sample chamber and the electrode plate in a height direction, to form a second gap between a second inner side wall of the sample chamber and the electrode in a width direction, and to form a third gap between a third inner side wall of the sample chamber and the electrode in the width direction, and
   wherein a size of each of the first gap, the second gap, and the third gap substantially define a gain of the electrode.

2. The cooking medium filter system of claim 1, wherein the sample chamber comprises a lower opening formed therein, the lower opening formed near a floor of the sample chamber,
   wherein the sample chamber comprises an upper opening formed therein, the upper opening formed near a top of the sample chamber and disposed in the filter path downstream from the lower opening,
   wherein the sample chamber is configured to receive the cooking medium via the lower opening, and
   wherein the sample chamber is configured to discharge the cooking medium via the upper opening.

3. The cooking medium filter system of claim 1, wherein the sample chamber is disposed in the filter path downstream from the filter medium and upstream of the pump.

4. The cooking medium filter system of claim 1, wherein the size of each of the first gap, the second gap, and the third gap is based on at least one of the height, width, and thickness of the electrode plate.

5. The cooking medium filter system of claim 1, wherein the electrode further comprises a conductor that is fixed to the first inner side wall of the sample chamber and disposed above the electrode plate to form a fourth gap between the conductor and the electrode,
   wherein a size of the fourth gap is based on at least one of the height, width, and thickness of the electrode plate, and the size of each of the first gap, the second gap, the third gap, and the fourth gap substantially define the gain of the electrode.

6. The cooking medium filter system of claim 1, wherein the sample chamber further comprises a temperature sensor disposed therein,
   wherein the sample chamber is configured to receive therein a second quantity of the cooking medium sufficient to immerse the electrode and the temperature sensor therein, and
   wherein the controller is configured to control the temperature sensor to measure a temperature of the cooking medium.

7. The cooking medium filter system of claim 6, wherein the property measured by the electrode is a conductivity of the cooking medium, and
   wherein the controller is configured to determine the quality of the cooking medium at a particular temperature based on the measured temperature of the cooking medium and the measured conductivity of the cooking medium.

8. The cooking medium filter system of claim 1, wherein the controller is configured to control the pump to pause conveyance of the cooking medium along the filter path for a particular period of time, and wherein the controller is configured to control the electrode to measure the property of the cooking medium during the particular period of time.

9. The cooking medium filter system of claim 1, wherein the property measured by the electrode is a capacitance of the cooking medium, and
wherein the controller is configured to determine the quality of the cooking medium based on the measured capacitance of the cooking medium.

10. The cooking medium filter system of claim 1, wherein the sample chamber comprises a level sensor configured to determine that the electrode is immersed in the cooking medium,
wherein the level sensor is configured to notify the controller when the level sensor determines that the electrode is immersed in the cooking medium, and
wherein the controller is further configured to control the electrode to measure the property of the cooking medium when the controller receives a notification from the level sensor that the electrode is immersed in the cooking medium.

11. The cooking medium filter system of claim 1, wherein the cooking medium filter system further comprises a pressure transducer disposed at an outlet of the pump,
wherein the pressure transducer is configured to determine that the sample chamber has received the first quantity of cooking medium,
wherein the pressure transducer is configured to notify the controller when the pressure transducer determines that the sample chamber has received the first quantity of the cooking medium, and
wherein the controller is further configured to control the electrode to measure the property of the cooking medium when the controller receives a notification from the pressure transducer that the sample chamber has received the first quantity of the cooking medium.

12. A cooking medium filter system configured to determine a quality of a cooking medium, the cooking medium filter system comprising:
a filter container configured to receive the cooking medium from a cooking vessel;
a filter medium disposed in the filter container and configured to remove contaminants from the cooking medium received in the filter container;
a pump configured to convey the cooking medium along a filter path from the filter container to the cooking vessel;
a sample chamber disposed in the filter path downstream from the filter medium, the sample chamber comprising an electrode disposed therein, and the sample chamber configured to receive therein a first quantity of the cooking medium that is sufficient to immerse the electrode therein, wherein the sample chamber comprises a U-shaped trap; and
a controller configured to control operations of the pump and configured to control the electrode to measure a property of the cooking medium that is associated with the quality of the cooking medium.

13. A method for monitoring a quality of a cooking medium conveyed through a cooking medium filter system, the method comprising:
receiving the cooking medium in a filter container from a cooking vessel;
activating a pump to convey the cooking medium along a filter path from the filter container to the cooking vessel;
removing contaminants from the received cooking medium;
supplying a first quantity of the cooking medium to a sample chamber that is sufficient to immerse an electrode disposed in the sample chamber;
determining that the electrode is immersed in the cooking medium;
deactivating the pump in response to determining that the electrode is immersed in the cooking medium, such that conveyance of the cooking medium along the filter path is paused for a particular period of time; and
measuring a property of the cooking medium in the sample chamber with the electrode during the particular period of time in response to the pump being deactivated to pause conveyance of the cooking medium along the filter path, the property being associated with the quality of the cooking medium.

14. The method of claim 13, further comprising:
supplying the first quantity of the cooking medium to the sample chamber via a lower opening formed in the sample chamber near a floor thereof; and
discharging the cooking medium from the sample chamber via an upper opening formed near a top of the sample chamber and disposed in the filter path downstream from the lower opening.

15. The method of claim 13, further comprising:
supplying a second quantity of the cooking medium to the sample chamber that is sufficient to immerse the electrode and a temperature sensor disposed in the sample chamber;
determining that the temperature sensor is immersed in the cooking medium; and
measuring a temperature of the cooking medium in the sample chamber with the temperature sensor during the particular period of time in response to the pump being deactivated,
wherein deactivating the pump in response to determining that the electrode is immersed in the cooking medium comprises deactivating the pump in response to determining that both the electrode and temperature sensor are immersed in the cooking medium.

16. The method of claim 15, wherein the property measured by the electrode is a conductivity of the cooking medium, and
wherein the method further comprises determining the quality of the cooking medium at a particular temperature based on the measured temperature of the cooking medium and the measured conductivity of the cooking medium.

17. The method of claim 13, wherein the property measured by the electrode is a capacitance of the cooking medium, and
wherein the method further comprises determining the quality of the cooking medium based on the measured capacitance of the cooking medium.

18. The method of claim 13,
wherein determining that the electrode is immersed in the cooking medium is performed using a level sensor.

19. The method of claim 13,
wherein the first quantity of cooking medium is sufficient to immerse the electrode and a temperature sensor disposed in the sample chamber, and
wherein the method further comprises measuring a temperature of the cooking medium in the sample chamber with the temperature sensor when the temperature sensor is immersed in the sample chamber.

20. A method for monitoring a quality of a cooking medium conveyed through a cooking medium filter system, the method comprising:

receiving the cooking medium in a filter container from a cooking vessel;

activating a pump to convey the cooking medium along a filter path from the filter container to the cooking vessel;

removing contaminants from the received cooking medium;

supplying a particular quantity of the cooking medium to a sample chamber that is sufficient to immerse an electrode disposed in the sample chamber;

measuring a property of the cooking medium in the sample chamber with the electrode, the property being associated with the quality of the cooking medium;

determining that the particular quantity of cooking medium is supplied to the sample chamber using a pressure transducer, and measuring the property of the cooking medium with the electrode when it is determined that the particular quantity of the cooking medium is supplied to the sample chamber.

21. A fryer system configured to determine a quality of a cooking medium, the fryer system comprising:

a cooking vessel configured to receive the cooking medium therein;

a cooking medium filter system configured to filter the cooking medium, the cooking medium filter system comprising:

a filter container configured to receive the cooking medium from the cooking vessel;

a filter medium disposed in the filter container and configured to remove contaminants from the cooking medium received in the filter container;

a pump configured to convey the cooking medium along a filter path from the filter container to the cooking vessel; and a sample chamber disposed in the filter path downstream from the filter medium, the sample chamber comprising an electrode and a temperature sensor disposed therein, and the sample chamber configured to receive therein a quantity of the cooking medium that is sufficient to immerse the electrode and the temperature sensor therein; and a controller configured to:

determine that the electrode and the temperature sensor are both immersed in the cooking medium, control the pump to pause conveyance of the cooking medium along the filter path for a particular period of time in response to determining that the electrode and the temperature sensor are both immersed in the cooking medium, control the temperature sensor to measure a temperature of the cooking medium during the particular period of time in response to the pump being controlled to pause conveyance of the cooking medium along the filter path, control the electrode to measure a conductivity of the cooking medium during the particular period of time in response to the pump being controlled to pause conveyance of the cooking medium along the filter path, and determine the quality of the cooking medium at a particular temperature based on the measured temperature of the cooking medium and the measured conductivity of the cooking medium during the particular period of time.

22. The fryer system of claim 21, wherein the electrode comprises:

an electrode plate comprising a first side and a second side opposite the first side, the electrode plate configured to be immersed in the first quantity of cooking medium, the electrode plate having a height, a width, and a thickness; and an insulator formed on the first side of the electrode plate and covering a surface of the electrode defined by the height and the width, wherein the insulator is fixed to a first inner side wall of the sample chamber, and wherein the electrode is disposed within the sample chamber to form a first gap between a floor of the sample chamber and the electrode plate in a height direction, to form a second gap between a second inner side wall of the sample chamber and the electrode in a width direction, and to form a third gap between a third inner side wall of the sample chamber and the electrode in the width direction, and wherein a size of each of the first gap, the second gap, and the third gap substantially define a gain of the electrode.

* * * * *